United States Patent [19]

Ganguly et al.

[11] Patent Number: 5,763,600
[45] Date of Patent: Jun. 9, 1998

US005763600A

[54] OLIGOSACCHARIDE ANTIBIOTICS AND PROCESS FOR PREPARATION THEREOF

[75] Inventors: Ashit Ganguly, Upper Montclair; Jinping L. McCormick, Edison; Anil K. Saksena, Upper Montclair; Tze-Ming Chan, Bridgewater, all of N.J.

[73] Assignee: Schering Corporation, Kenilworth, N.J.

[21] Appl. No.: 844,487

[22] Filed: Apr. 18, 1997

[51] Int. Cl.$^6$ .............. C07H 3/06; C07H 3/08; A61K 31/715

[52] U.S. Cl. .............. 536/123; 536/4.1; 536/17.2; 536/17.7; 536/123.1; 514/25; 514/54

[58] Field of Search .............. 514/25, 54; 536/4.1, 536/17.2, 17.7, 123, 123.1

[56] References Cited

U.S. PATENT DOCUMENTS

| | | | |
|---|---|---|---|
| 3,915,956 | 10/1975 | Ganguly et al. | 536/16.8 |
| 4,006,225 | 2/1977 | Ganguly et al. | 514/25 |
| 4,129,720 | 12/1978 | Ganguly et al. | 536/17 |
| 4,597,968 | 7/1986 | Waitz et al. | 424/118 |
| 4,622,314 | 11/1986 | Ganguly et al. | 514/54 |
| 4,767,748 | 8/1988 | Ganguly et al. | 514/54 |
| 5,624,914 | 4/1997 | Patel et al. | 514/54 |
| 5,652,226 | 7/1997 | Girijavallabhan et al. | 514/54 |

FOREIGN PATENT DOCUMENTS

| | | |
|---|---|---|
| 28 05 408 | 8/1978 | Germany. |
| WO87/02366 | 4/1987 | WIPO. |
| 97/13777 | 4/1997 | WIPO. |

OTHER PUBLICATIONS

Ganguly et al., *Heterocycles*, vol. 28, No. 1: 83–88, 1989.
Jütten et al., *J. Org. Chem.*, vol. 56: 7144–7149, 1991.
Nakashio et al., *Drugs Exptl. Clin. Res.*, vol. XXI(1): 7–16, 1995.
Ganguly et al., *Journal of Antibiotics*, vol. XXXV(5): 561–570, May 1982.
Sutter et al., *Antimicrobioal Agents and Chemotherapy*; vol. 10, No. 4, pp. 736–752, 1976.
Ganguly, A. K., et al. Kirk–Othmer, Encyclopedia of Chemical Technology, (1978), 3rd Ed., vol. 2, 986–990.
Girijavallabhan, V.M., Ganguly, A.K., Kirk–Othmer, Encyclopedia of Chemical Technology (1992) 4th Ed. vol. 3,259–266.
Derek E. Wright, Tetrahedron Report No. 62, The Orthosomycins a New Family of Antibiotics, Tetrahedron vol. 35, Pergamon Press Ltd., (1979), pp. 1207–1237.

*Primary Examiner*—John Kight
*Assistant Examiner*—Howard C. Lee
*Attorney, Agent, or Firm*—Joseph T. Majka

[57] ABSTRACT

Novel oligosaccharide antibiotics of formula I and I' are disclosed, together with a method for their preparation.

19 Claims, No Drawings

OLIGOSACCHARIDE ANTIBIOTICS AND PROCESS FOR PREPARATION THEREOF

BACKGROUND

Orthosomycins are a group of complex oligosaccharide antibiotics which include everninomicins, the flambamycins, the avilamycins and the curamycins. A unique structural feature shared among these antibiotics is the presence of two orthoester bonds at carbon numbers 16 and 49, i.e. (C 16) and (C49). Such oligosaccharide antibiotics are active against Gram positive bacteria including methicillin resistant *Staphylococci* and vancomycin resistant *Enterococci*. V. M. Girijavallabhan & A. K. Ganguly, Kirk-Othmer Encyclopedia of Chemical Technology, 4th Ed., Vol. No. 3, pp. 259–266, reported structures of several everninomicins, flambamycins, avilamycins and curamycins The orthoester bonds at the C16 position of these antibiotics tend to be relatively more susceptible than the orthoesters at C49 to hydrolysis (i.e. degradation by cleavage) in the presence of acids, such as hydrochloric acid produced by the stomach, resulting in complete loss of antibiotic activity. Therefore, a preferable mode of administration of these antibiotics is via the intravenous mode. Any means to make these useful antibiotics more stable to acidic pH may provide greater flexibility in terms of their administration via oral as well as intravenous routes. Thus, it would be highly desirable to obtain more stable oligosaccharide antibiotics whose orthoester bonds at the C16 position are more stable to acids. It would also be desirable to provide a method for preparing a variety of oligosaccharide antibiotics of this class which are more stable under acid conditions.

SUMMARY OF THE INVENTION

During our studies with these oligosaccharide antibiotics, we have discovered unexpected isomerization of the orthoester at the C16 position, providing new oligosaccharide antibiotics of formula I and I'

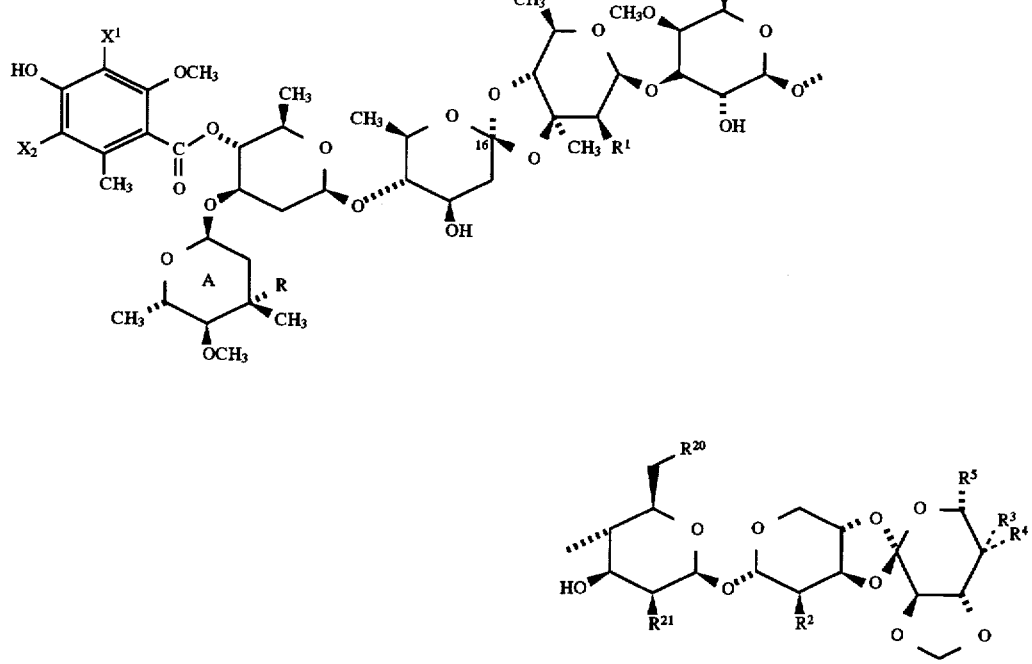

and

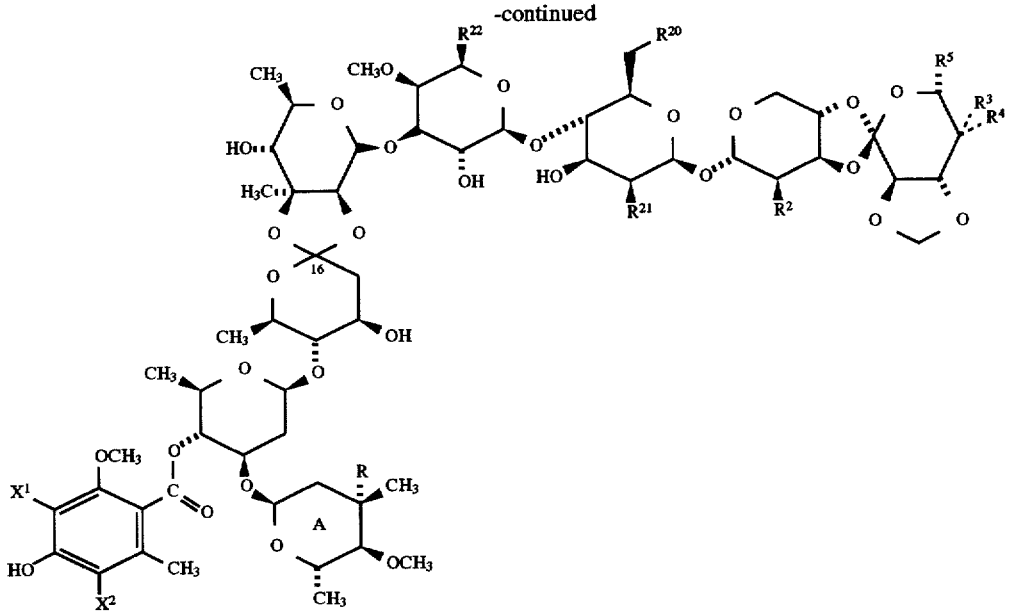

wherein

X¹ and X² independently represent hydrogen or chloro, provided at least one of X¹ and X² is chloro;

Ring A is as shown or is hydrogen;

R is —OH, —NO$_2$, —NH$_2$, —NR$^6$R$^7$ or —NHC(O)CHR$^8$R$^9$, wherein

R$^6$ is hydrogen or alkyl,

R$^7$ is hydrogen or alkyl,

R$^8$ is hydrogen or —NR$^6$R$^7$, wherein R$^6$ and R$^7$ are defined hereinabove, R$^9$ is hydrogen, alkyl or an amino acid side chain, wherein R$^{10}$ is hydrogen or alkyl, R$^{11}$ is hydrogen or alkyl;

R$^1$ is hydrogen or —OH;

R$^2$ is —OH or —OR$^{12}$, wherein

R$^{12}$ is alkyl or C(O)R$^{13}$, wherein

R$^{13}$ is alkyl;

R$^3$ is hydrogen,

—OH, —CHOCH$_3$, —C(O)R$^{14}$, —CH(OH)R$^{15}$ or
        |
        CH$_3$

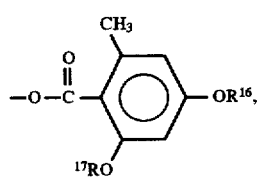

wherein

R$^{14}$ is hydrogen or alkyl,

R$^{15}$ is alkyl,

R$^{16}$ is hydrogen, alkyl or alkenyl,

R$^{17}$ is hydrogen, alkyl or alkenyl,

R$^4$ is hydrogen or OH;

R$^5$ is hydrogen or methyl;

R$^{20}$ is —OH or —OCH$_3$;

R$^{21}$ is —OH or —OCH$_3$;

R$^{22}$ is hydrogen, —CH$_3$ or —CH$_2$OH;

and pharmaceutically acceptable salts thereof.

Preferably, X¹ and X² are chloro. Also preferred is that R is —NO$_2$ or —NHC(O)CH$_3$. Preferably, R$^1$ is hydrogen or —OH. Also preferred is that R$^2$ is —OH, —OCH$_3$ or —OCH$_2$CH$_2$OH.

Preferably R$^3$ is

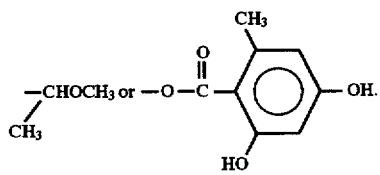

Also preferred is that R$^4$ is hydrogen or —OH. Preferably, R$^5$ is hydrogen. Also preferred is that R$^{20}$ and R$^{21}$ are —OCH$_3$ and R$^{22}$ is —CH$_3$.

These new oligosaccharide antibiotics have the advantage of being significantly more stable to acids than their respective parent oligosaccharide antibiotics of formula II.

The present invention is also directed to a process for preparing the oligosaccharide antibiotics of formulas I and I'. The method comprises contacting oligosaccharide compound of the formula:

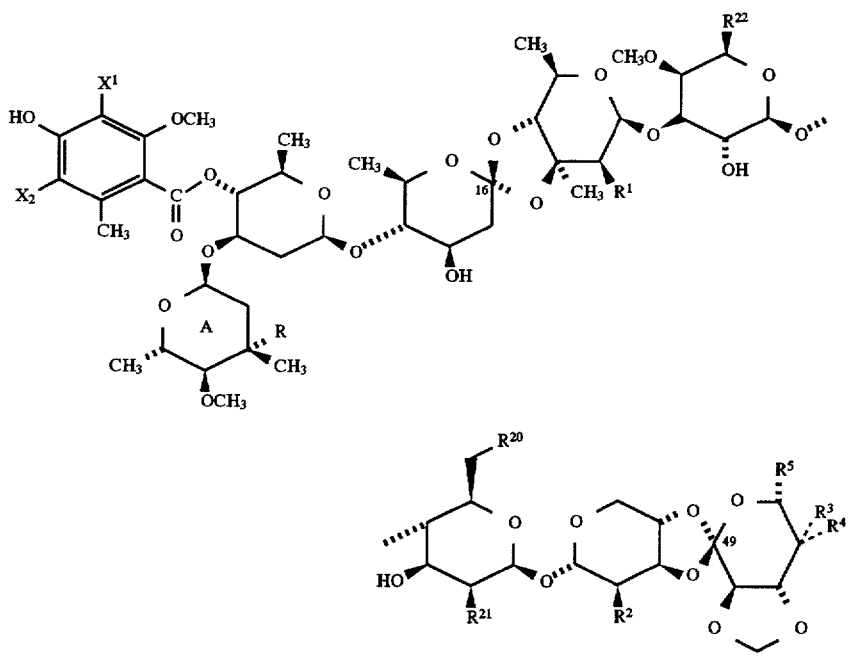

wherein R, $R^1$, $R^2$, $R^3$, $R^4$, $R^5$, $R^{20}$, $R^{21}$ and $R^{22}$ are defined above, with an organic acid and a non-protic solvent under anhydrous conditions to form the oligosaccharide antibiotics of formula I and I'. Preferably, the organic acid is p-nitrobenzoic acid and the solvent is tetrahydrofuran.

DETAILED DESCRIPTION OF THE INVENTION

The following solvents and reagents are referred to herein by the abbreviations indicated:

tetrahydrofuran (THF);

ethanol (EtOH);

methanol (MeOH);

ethyl acetate (EtOAc);

N,N-dimethylformamide (DMF);

dichloromethane ($CH_2Cl_2$);

acetic acid (HOAc or AcOH)

acetoxy or O-acetyl (OAc)

As used herein, the following terms are used as defined below unless otherwise indicated:

▲ or ⋰⋰⋰—indicates a pure enantiomer;

——when attached to a carbon atom labeled with an asterisk (*), indicates a separated isomer whose stereochemistry is not established;

⁓—indicates a bond whose stereochemistry can be either in the R or S stereoconfiguration;

M+—represents the molecular ion of the molecule in the mass spectrum;

MH+—represents the molecular ion plus hydrogen of the molecule in the mass spectrum;

PMR or NMR refers to proton magnetic resonance spectroscopy or nuclear magnetic resonance spectroscopy, whose terms are interchangeable;

Bu—represents butyl;

Et—represents ethyl;

Me—represents methyl;

Ph—represents phenyl;

Me—represents methyl;

OMe—represents methoxy.

Amino acid side chain-represents an organic compound marked by the presence of both an amino group ($NH_2$) and a carboxyl group (COOH). Their basic formula is $NH_2$—Y—COOH in which Y stands for an amino acid side chain, such as an alkyl, aryl or aralkyl group, which will complete the amino acid. Examples of naturally occuring amino acids side chains include those Y groups which will give amino acids such as alanine, aspartic acid, arginine, citrulline, cysteine, cystine, glutamic acid, glycine, histidine, hydroxyglutamic acid, hydroxyproline, isoleucine, leucine, lysine, methionine, norleucine, phenylalanine, proline, serine, threonine, tryptophan, tyrosine and valine.

alkyl (including alkyl portions of alkoxy, alkylamino, dialkylamino, heterocycloalkyl and $R^{10}$) represents straight and branched carbon chains and contains from one to six carbon atoms (i.e. $C_1$-$C_6$); for example methyl, ethyl, propyl, iso-propyl, n-butyl, n-pentyl, isopentyl, hexyl and the like; wherein said alkyl group may be optionally and independently substituted with one or two of the following: alkyl, alkoxy, aryl, cycloalkyl, cyano, —$CF_3$, oxy (=O), aryloxy, —$OR^{10}$, —$OCF_3$, halo, heterocycloalkyl, heteroaryl, —$NR^{10}R^{18}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{18}$ are independently selected from hydrogen, alkyl or aryl.

alkenyl—represents straight and branched carbon chains having at least one carbon to carbon double bond and containing from 2 to 12 carbon atoms, preferably from 2 to 6 carbon atoms and most preferably from 3 to 6 carbon atoms; wherein said alkenyl group may be optionally and independently substituted with one, two, three or more of the following: alkyl, alkoxy, aryl, cycloalkyl, cyano, —$CF_3$, oxy (=O), aryloxy, —$OR^{10}$, —$OCF_3$, halo, heterocycloalkyl, heteroaryl, —$NR^{10}R^{18}$, —$NHSO_2R^{10}$, —$SO_2NH_2$, $SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{18}$ are defined above;

alkoxy—an alkyl moiety of one to 10 carbon atoms covalently bonded to an adjacent structural element through an oxygen atom, for example, methoxy, ethoxy, propoxy, butoxy, pentoxy, hexoxy and the like; wherein said alkoxy group may be optionally and independently substituted with one, two, three or more of the following: halo, alkyl, aryl, cycloalkyl, cyano, —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$, wherein R$^{10}$ and R$^{18}$ are defined above;

aryl (including the aryl portion of aralkyl)—represents a carbocyclic group containing from 6 to 15 carbon atoms and having at least one aromatic ring (e.g., aryl is phenyl), wherein said aryl group optionally can be fused with aryl, cycloalkyl, heteroaryl or heterocycloalkyl rings; and wherein any of the available substitutable carbon and nitrogen atoms in said aryl group and/or said fused ring(s) may be optionally and independently substituted with one, two, three or more of the following: alkyl, alkoxy, aryl, cycloalkyl, cyano, —CF$_3$, oxy (=O), aryloxy, —OR$^{10}$, —OCF$_3$, halo, heterocycloalkyl, heteroaryl, —NR$^{10}$R$^{18}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{18}$ are defined above;

aryloxy—represents an aryl group, as defined above, wherein said aryl group is covalently bonded to an adjacent structural element through an oxygen atom, for example, phenoxy, wherein said aryl group optionally can be fused with aryl, cycloalkyl, heteroaryl or heterocycloalkyl rings; and wherein any of the available substitutable carbon and nitrogen atoms in said aryloxy group and/or said fused ring(s) may be optionally and independently substituted with one, two, three or more of the following: halo, alkyl, alkoxy, aryl, cycloalkyl, cyano, —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, OCO$_2$R$^{10}$ or —COOR$^{10}$, wherein R$^{10}$ and R$^{18}$ are defined above;

cycloalkyl—represents saturated carbocyclic rings branched or unbranched of from 3 to 20 carbon atoms, preferably 3 to 7 carbon atoms; wherein said cycloalkyl group may be optionally and independently substituted with one, two, three or more of the following: halo, alkyl, alkoxy, aryl, cycloalkyl, cyano, —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{18}$ are defined above;

halo—bromo, chloro, iodo or fluoro;

heteroaryl—represents cyclic groups having at least one heteroatom selected from O, S and N, said heteroatom(s) interrupting a carbocyclic ring structure and having a sufficient number of delocalized pi electrons to provide aromatic character, with the aromatic heterocyclic groups containing from 2 to 14 carbon atoms, wherein said heteroaryl group optionally can be fused with one or more aryl, cycloalkyl, heteroaryl or heterocycloalkyl rings; and wherein any of the available substitutable carbon or nitrogen atoms in said heteroaryl group and/or said fused ring(s) may be optionally and independently substituted with one, two, three or more of the following: halo, alkyl, alkoxy, aryl, cycloalkyl, cyano, —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{18}$ are defined above;

heterocycloalkyl—represents a saturated, branched or unbranched carbocylic ring containing from 3 to 15 carbon atoms, preferably from 4 to 6 carbon atoms, which carbocyclic ring is interrupted by 1 to 3 heteroatoms selected from —O—, —S— and —N—, wherein optionally, said ring may contain one or two unsaturated bonds which do not impart aromatic character to the ring; and wherein any of the available substitutable carbon and nitrogen atoms in the ring may be optionally and independently substituted with one, two, three or more of the following: halo, alkyl, alkoxy, aryl, cycloalkyl, cyano, —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{18}$ are defined above. Representative heterocycloalkyl groups can include 2- or 3-tetrahydrofuranyl, 2- or 3-tetrahydrothienyl, 1-, 2-, 3- or 4-piperidinyl, 2- or 3-pyrrolidinyl, 1-, 2- or 3-piperizinyl, 2- or 4-dioxanyl, morpholinyl,

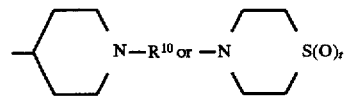

wherein R$^{10}$ is defined hereinbefore and t is 0, 1 or 2.

Certain oligosaccharide antibiotics of the present invention may exist in different stereoisomeric forms (e.g., enantiomers and diastereoisomers). The invention contemplates all such stereoisomers both in pure form and in mixture, including racemic mixtures.

Certain oligosaccharide antibiotics of formula I and I' will be acidic in nature, e.g. those compounds which possess a carboxyl or phenolic hydroxyl group. These compounds can form pharmaceutically acceptable salts. Examples of such salts may include sodium, potassium, calcium and aluminum salts. Also contemplated are salts formed with pharmaceutically acceptable amines such as ammonia, alkyl amines, hydroxyalkylamines, N-methylglucamine and the like.

Certain basic compounds can also form pharmaceutically acceptable salts, e.g., acid addition salts. For example, compounds having basic substituents such as amino groups also form salts with a suitable acid. Examples of suitable acids for salt formation are phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable within the scope of the invention and all acid and base salts are considered equivalent to the free forms of the corresponding compounds for purposes of the invention.

The oligosaccharide antibiotics of the present invention can be prepared as follows.

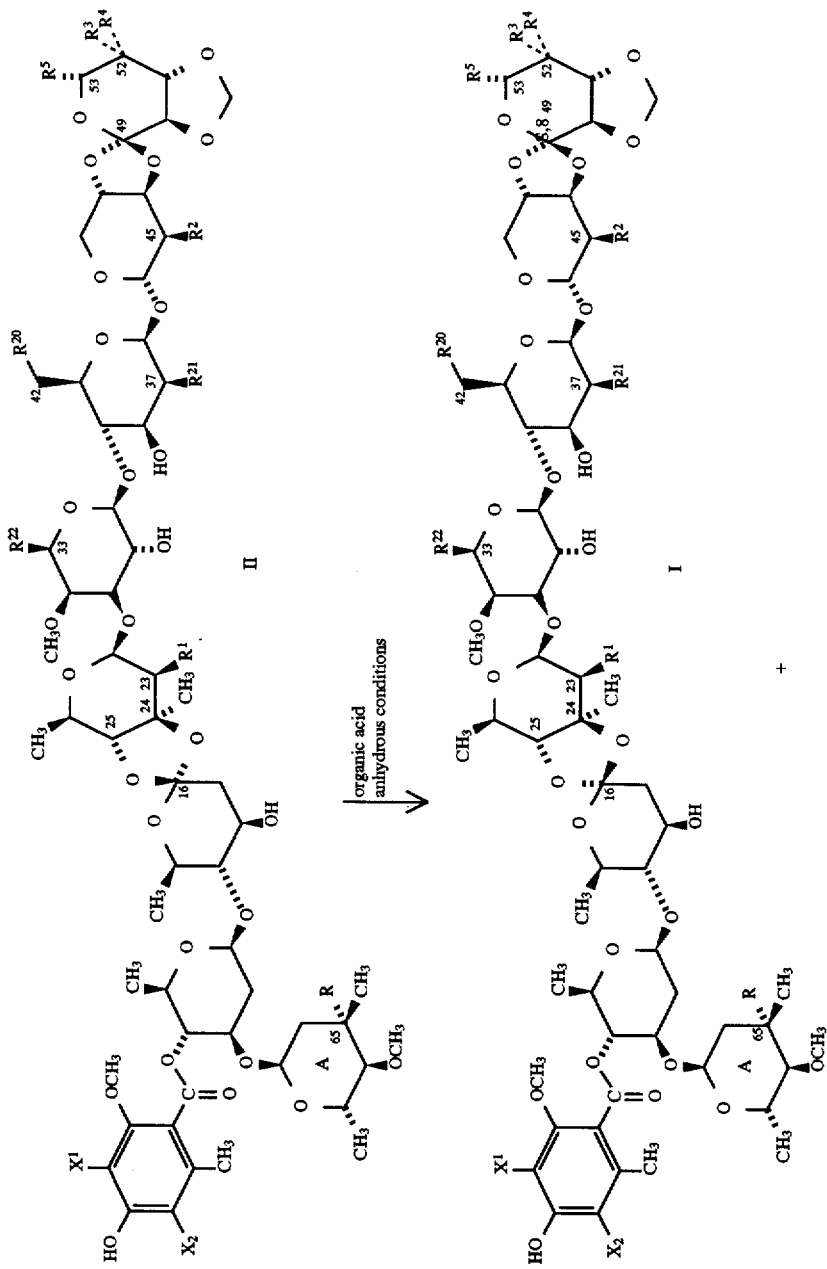

-continued
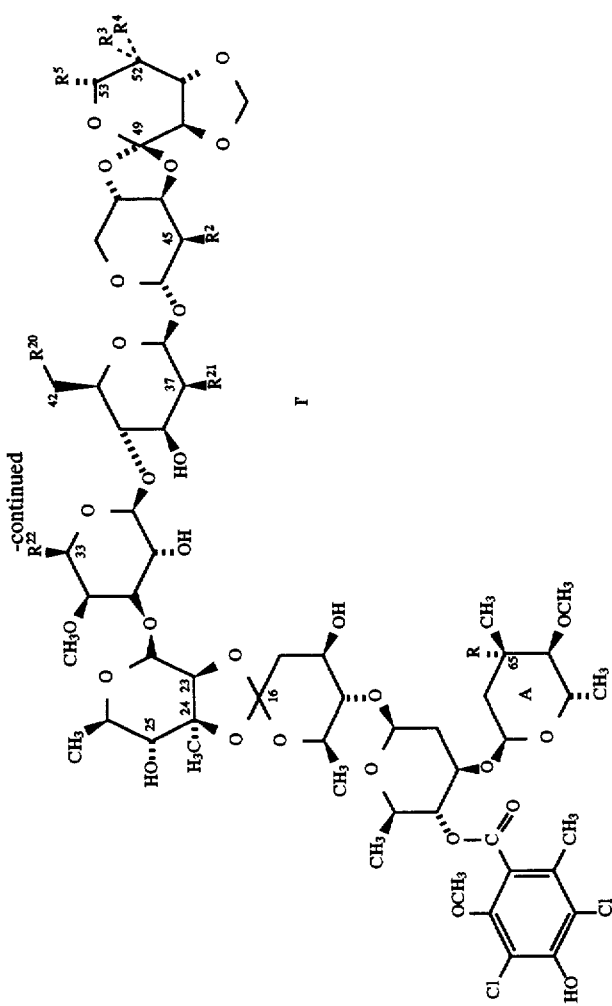

wherein R, R¹, R², R³, R⁴, R⁵, R²⁰, R²¹ and R²² are defined hereinabove. In the above scheme a parent oligosaccharide antibiotic of formula II is contacted with an organic acid and an aprotic solvent under anhydrous conditions to form the oligosaccharide antibiotic of formula I and I'. One of ordinary skill in the art will recognize that when R¹ (bonded to C23) in oligosaccharide antibiotic II is hydrogen, only oligosaccharide antibiotic I is obtained. Preferably, R³ in oligosaccharide antibiotics I, I' and II has the ⫽ stereoconfiguration.

An organic acid is an organic compound containing a dissociable proton and having a pKa of zero to five, preferably a pKa of 3.5 to 5.0. Suitable organic acids include those of the formula R¹⁰COOH, wherein R¹⁰ is hydrogen, alkyl, aryl or aralkyl, as defined hereinbefore. Representative organic acids include alkylated acids such as propionic acid and butyric acid; benzoic acid, substituted benzoic acids such as p-nitrobenzoic acid; acetic acid, acetic acid substituted with alkyl or aryl moieties; and mixtures thereof. The organic acid is used in amounts sufficient to isomerize oligosaccharide antibiotic II to oligosaccharide antibiotics I and I'. Such amounts can range from catalytic to excess moles of organic acid per mole of oligosaccharide antibiotic II, preferably from about equimolar to about three moles of organic acid per mole of antibiotic II.

The non-protic solvent should be substantially inert in the reaction mixture. Suitable non-protic solvents include THF, acetonitrile, dichloromethane, chloroform, and ethers such as diethylether and t-butylmethyl ether. The solvent can be used in amounts sufficient to solubilize the reactants in the reaction mixture.

The reactants are contacted for a time sufficient to form the desired oligosaccharide antibiotic I or I', such as from three to four hours to about two days. Generally, a longer reaction time tends to favor formation of oligosaccharide antibiotic I', whereas a shorter reaction time tends to favor formation of oligosaccharide antibiotic I.

The reactants can be contacted at temperatures ranging from ambient to about the reflux temperature of the non-protic solvent and/or reaction mixture, preferably from about 20° C. to about 100° C., more preferably from about 50° C. to about 85° C.

It is extremely desirable that the reactants are contacted under anhydrous (water-free) conditions, since the presence of water can encourage hydrolysis of the oligosaccharide antibiotic II reactant.

The oligosaccharide antibiotics of fomula (I and I') can be recovered or isolated from the reaction mixture using conventional procedures, such as, for example, extraction of the reaction mixture from water with organic solvents, evaporation of the organic solvents, followed by chromatography on silica gel, on column or on other suitable chromatographic media.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 50 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration. Liquid form preparations include solutions, suspensions and emulsions. As an example may be mentioned water or water-propylene glycol solutions for parenteral injection.

For example, the oligosaccharide antibiotics of formula I and I' are prepared for intravenous injection, using formulations such as those described in International Application No. PCT/US92/08565. For example, such formulations can include (a) a lipophilic oligosaccharide antibiotic such as the present everninomicins of formula I and I', (b) at least about a stoichiometric amount of a base capable of forming a pharmaceutically acceptable salt with the lipophilic oligosaccharide antibiotic, (c) an amount of dimethylsulfoxide, glycerol, a sorbitan mono-9-octadecenoate poly(oxy-1,2-ethanediyl)derivative, dextran, a hydroxypropyl-α-, -β- or -γ-cyclodextrin wherein the average number of hydroxypropyl substituents on said α-, β- and γ-cyclodextrin is in the range of about 2 to about 15, and said amount is sufficient to achieve efficacious delivery of said lipophilic oligosaccharide antibiotic to the serum of a mammal; and optionally and preferably, (d) 0 to 6.0% by weight (basis, the antibiotic of Formula I and I') of a pharmaceutically acceptable non-ionic surfactant, and and (e) mannitol. Also preferred is that the molar ratio of (a):(b):(c) is 1:3:5 and the weight percent of the polysorbate 80 (basis the compound of formula I and I') is about 2.85 and the weight percent of mannitol (basis whole composition) is about 18.1%.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

Oligosaccharide antibiotics of the present invention and preparative starting materials therof, are exemplified by the following examples, which should not be construed as limiting the scope of the disclosure.

Example 1

Preparation of oligosaccharide antibiotic Ia

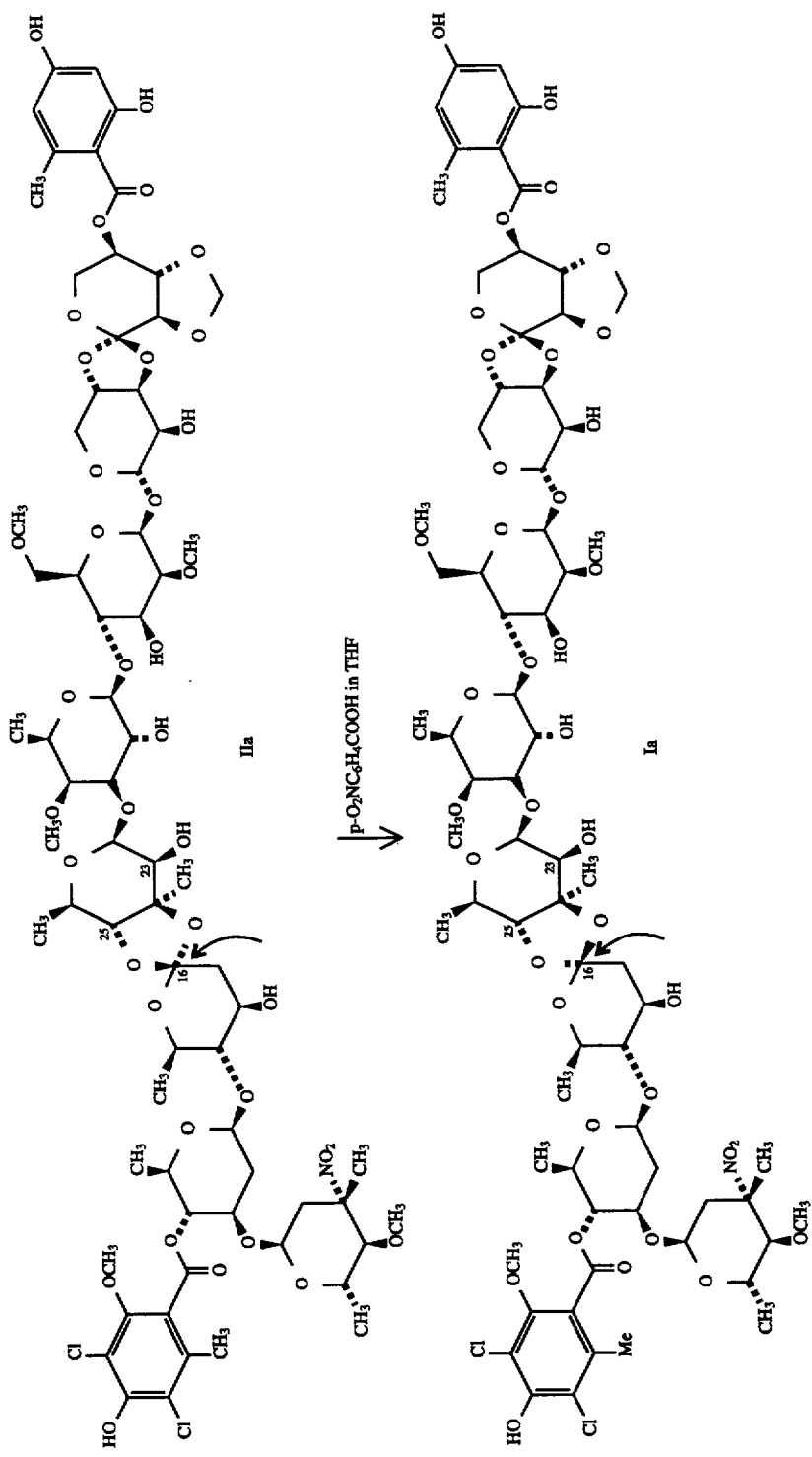

A solution containing oligosaccharide antibiotic IIa (976 mg, 0.599 mmol) and p-nitrobenzoic acid (300 mg, 1.796 mmol, 3.0 eq) in dry THF (20 mL) was kept at reflux for 16 hours (70° C., oil bath). Upon cooling, the solution was concentrated to a small volume and diluted with 100 mL of ethyl acetate (EtOAc). The solution was washed successively with aqueous sodium bicarbonate, water and brine, dried over sodium sulfate ($Na_2SO_4$), and concentrated to afford the crude product. Chromatography on silica gel (5% MeOH in $CH_2Cl_2$) gave predominantly oligosaccharide antibiotic Ia (212 mg, white solid): Rf 0.38 (7% MeOH—$CH_2Cl_2$) and a lesser amount of oligosaccharide antibiotic I'a (43 mg, white solid): Rf 0.31 (7% MeOH—$CH_2Cl_2$). Ia HRFABMS: 1652.4983 (M+Na, $C_{70}H_{97}Cl_2NO_{38}$, calc 1652.4963).

Acid stability of oligosaccharide antibiotic Ia and parent oligosaccharide antibiotic IIa The rate of hydrolysis or cleavage of the oligosaccharide antibiotics was studied in a biphasic system at room temperature, by treating parent oligosaccharide antibiotic II with 0.1 N HCl (aq)—EtOAc (1:4 v/v) and treating the resultant oligosaccharide antibiotic Ia with a more acidic media, 0.1N HCl (aq)—EtOAc (1:2 v/v) and monitoring the hydrolysis or degradation by thin layer chromatography. We found that after 4 hours treatment with acid, 50% of parent oligosaccharide antibiotic II had hydrolyzed, and after 7 hours, nearly 100% had hydrolyzed or degraded. In contrast, after 29 hours treatment with an even stronger acid, less than 50% of oligosaccharide antibiotic Ia was hydrolyzed, and 64 hours was required to achieve 100% hydrolysis or degradation. Such results clearly demonstrate the enhanced acid stability of oligosaccharide antibiotic Ia over its parent oligosaccharide antibiotic II.

EXAMPLE 2

Preparation of oligosaccharide antibiotic Ia

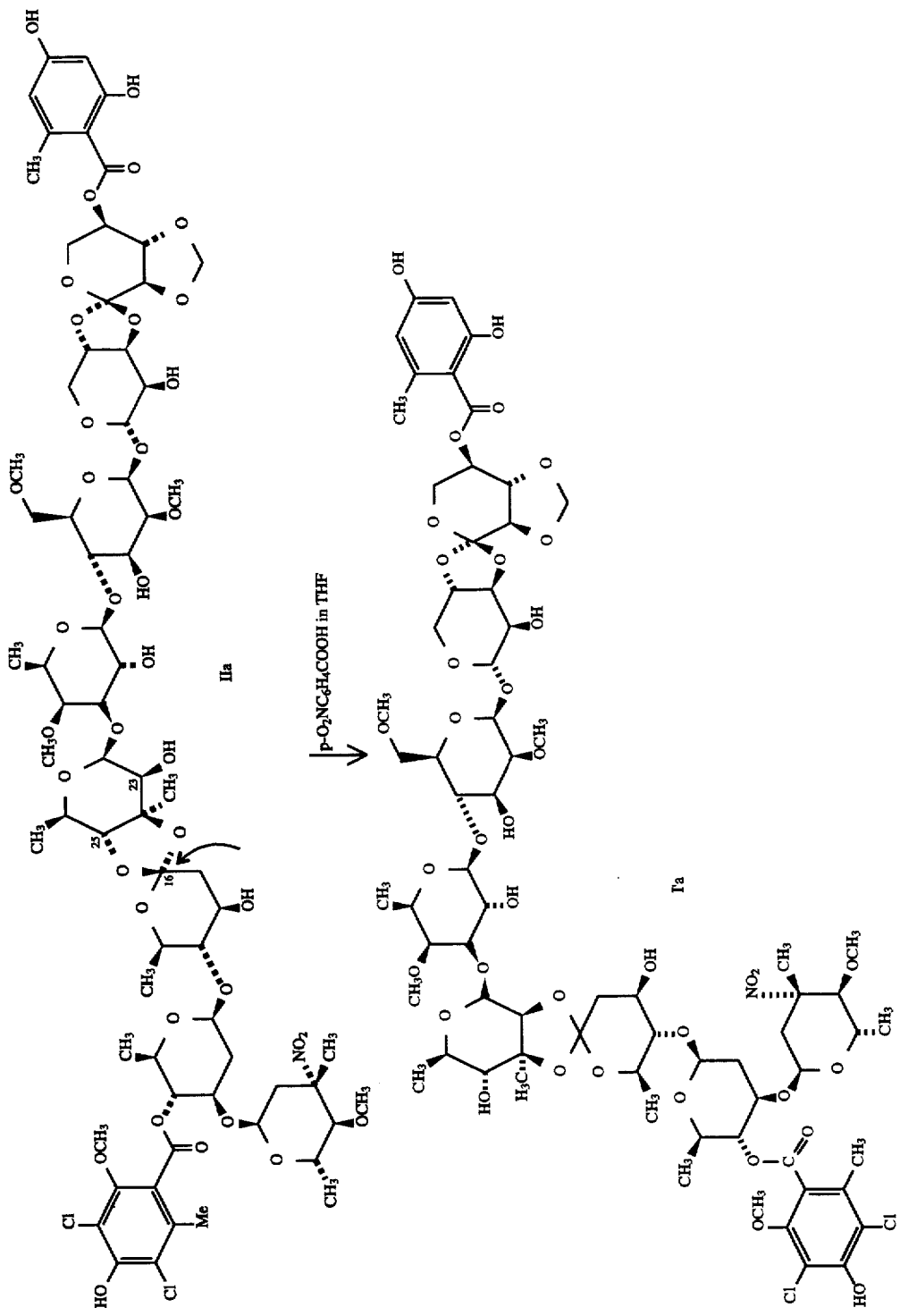

A solution containing oligosaccharide antibiotic IIa (1000 mg, 0.613 mmol) p-nitrobenzoic acid (304 mg, 1.820 mmol, 3.0 eq) in dry THF (20 mL) was kept at reflux for 44 h (70° C., oil bath). Upon cooling, the solvent was evaporated and the residue was dissolved in 100 mL of EtOAc. The solution was washed successively with aqueous sodium bicarbonate, water and brine, dried over $Na_2SO_4$, and concentrated to afford the crude product. Chromatography on silica gel (5% MeOH in $CH_2Cl_2$) gave predominantly oligosaccharide antibiotic I'a (224 mg, white solid) and a lesser amount of oligosaccharide antibiotic Ia (67 mg, white solid). I'a HRFABMS: 1652.4967 (M+Na, $C_{70}H_{97}Cl_2NO_{38}$, calc 1652.4963).

Acid stability of antibiotic I'a and antibiotic IIa

The rate of hydrolysis or cleavage of the oligosaccharide antibiotics was studied in a biphasic system at room temperature, by treating parent oligosaccharide antibiotic II with 0.1N HCl (aq)-EtOAc (1:4 v/v) and treating the resultant oligosaccharide antibiotic I'a with a more acidic media, 0.1 N HCl (aq)-EtAc (1:2 v/v) and monitoring the hydrolysis or degradation by thin layer chromatography. We found that after 4 hours treatment with acid, 50% of parent oligosaccharide antibiotic II had hydrolyzed, and after 7 hours, nearly 100% had hydrolyzed or degraded. In contrast, after 72 hours (3 days) treatment with an even stronger acid, less than 50% of oligosaccharide antibiotic I'a was hydrolyzed, and 168 hours (7 days) was required to achieve 100% hydrolysis or degradation. Such results clearly demonstrate the enhanced acid stability of oligosaccharide antibiotic I'a over its parent oligosaccharide antibiotic II.

EXAMPLE 3

Preparation of oligosaccharide antibiotic Ib

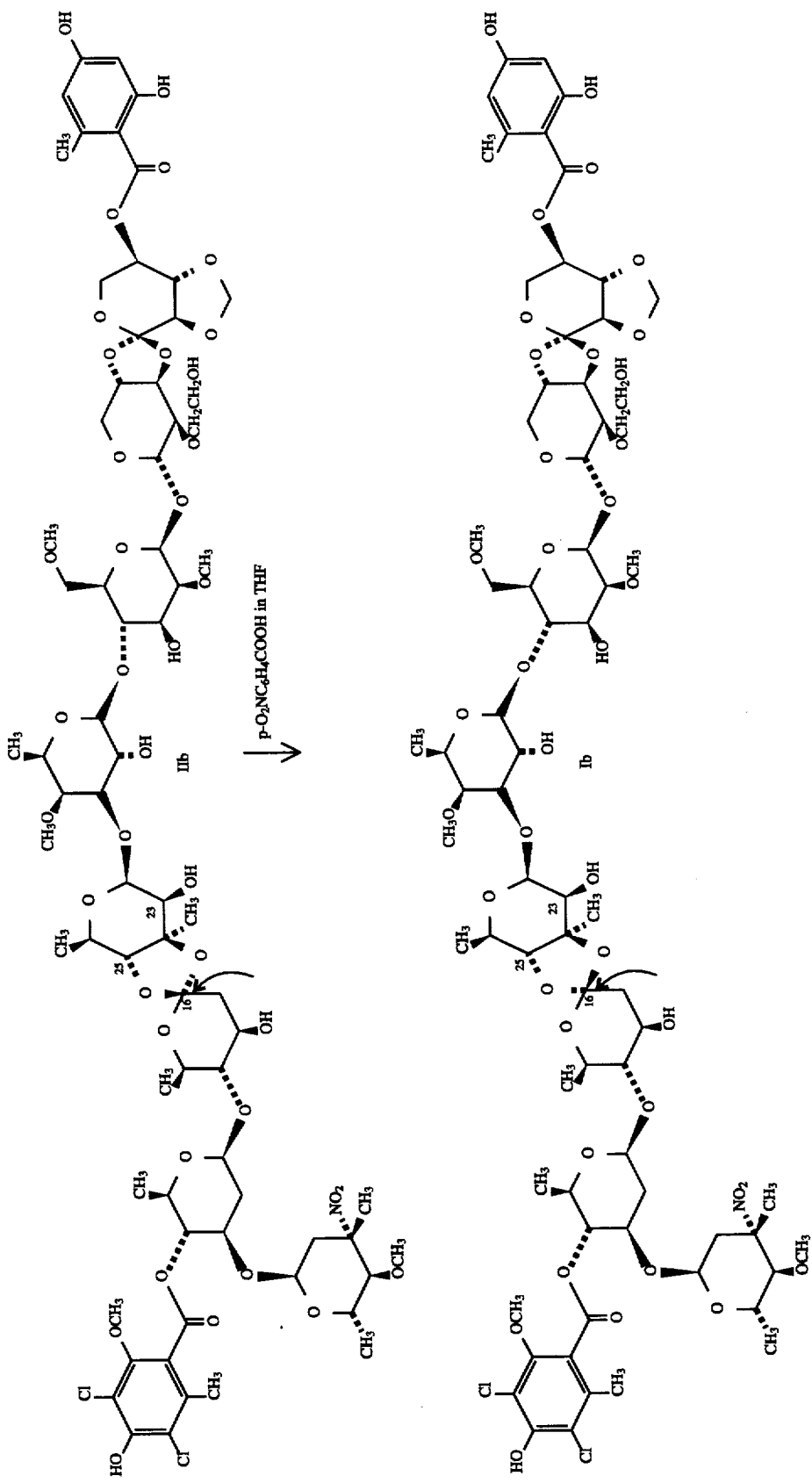

A solution containing oligosaccharide antibiotics IIb (99 mg, 0.0592 mmol) and p-nitrobenzoic acid (30 mg, 0.180 mmol, 3.0 eq) in 3 mL of dry THF was kept at reflux for 7 hours (70° C., oil bath). Upon cooling, the solution was concentrated to a small volume and diluted with 20 mL of EtOAc. The solution was washed successively with aqueous sodium bicarbonate, water and brine, dried over $Na_2SO_4$, and concentrated to afford the crude product. Chromatography on silica gel (5% MeOH in $CH_2Cl_2$) gave oligosaccharide antibiotic Ib (21 mg, white solid): Rf 0.41 (7% MeOH—$CH_2Cl_2$). HRFABMS: 1696.5221 (M+Na, $C_{72}H_{101}NO_{39}Cl_2Na$), calc 1696.5225.

EXAMPLE 4

Preparation of 65-acetamido oligosaccharide antibiotic Ic

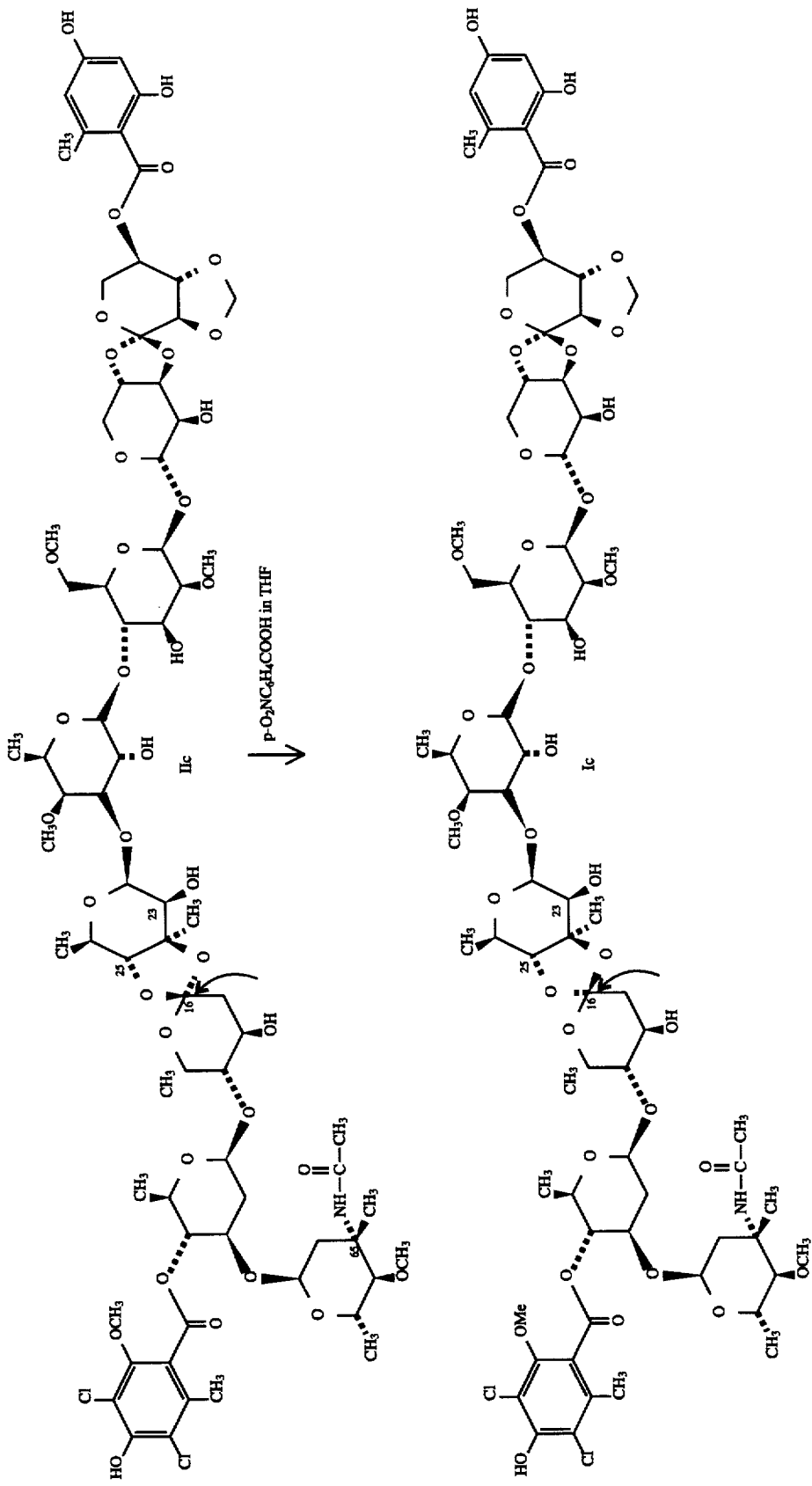

A solution containing oligosaccharide antibiotic IIc (54.7 mg, 0.0333 mmol) and p-nitrobenzoic acid (16.0 mg, 0.96 mmol, 2.9 eq) in dry THF (3 mL) was kept at reflux for 10 h (65° C., oil bath). Upon cooling, the solution was concentrated to a small volume and diluted with EtOAc (20 mL). The solution was washed successively with aqueous sodium bicarbonate, water and brine, dried over $Na_2SO_4$, and concentrated to afford the crude product. Chromatography on preparative silica gel plate (5% MeOH in $CH_2Cl_2$) gave oligosaccharide antibiotic Ic (13 mg, white solid): Rf 0.21 (7% MeOH—$CH_2Cl_2$). HRFABMS: 1664.5331 (M+Na, $C_{72}H_{101}NO_{37}Cl_2NA$), calc 1696.5327.

EXAMPLE 5

Preparation of everninomicin D antibiotic isomer Id

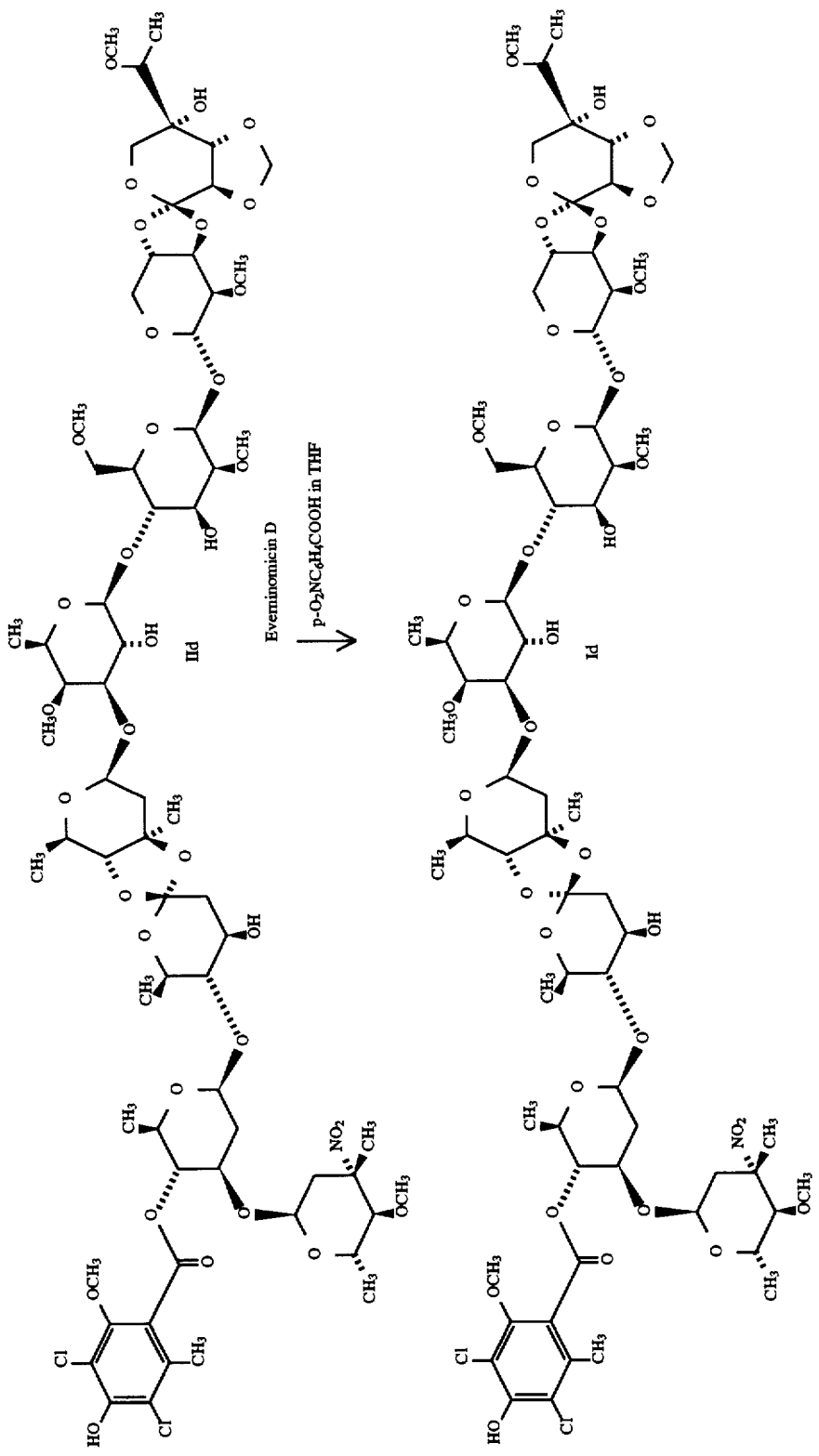

A solution containing everninomicin D-IId (51.2 mg, 0.0334 mmol) and p-nitrobenzoic acid (16.7 mg, 0.100 mmol, 3.0 eq) in 3 mL of dry THF was kept at reflux for 18 hours (70° C., oil bath). Upon cooling, the solution was concentrated to a small volume and diluted with 20 mL of EtOAc. The solution was washed successively with aqueous sodium bicarbonate, water and brine, dried over $Na_2SO_4$, and concentrated to afford the crude product. Chromatography on preparative silica gel plate (5% MeOH in $CH_2Cl_2$) gave antibiotic Id (11.3 mg, white solid): Rf 0.34 (5% MeOH—$CH_2Cl_2$). HRFABMS: 1558.5286 (M+Na, $C_{68}H_{103}NO_{34}Cl_2$, calc 1558.5272).

PREPARATION OF STARTING MATERIALS

The starting materials of formula II useful in preparing the oligosaccharide antibiotics of the present invention are known in the art and/or can be prepared using known methods, such as taught, for example, in A. K. Ganguly et al., The Structure of New Oligosaccharide Antibiotics, 13-384 Components 1 and 5, Heterocycles, Vol. 28, No.1, (1989), pp. 83–88; A. K. Ganguly et al., Chemical Modification of Everninomicins, The Journal of Antibiotics, Vol. XXXV No. 5, (1982), pp. 561–570; and V. M. Girijavallabhan & A. K. Ganguly, Kirk-Othmer Encyclopedia of Chemical Technology, 4th Ed., Vol. No. 3, (1992) pp. 259–266, Derek E. Wright, Tetrahedron Report Number 62, The Orthosomycins a New Family of Antibiotics, Tetrahedron Vol. 35, Pergamon Press Ltd., (1979), pp 1207–1237; and in references cited therein. Everninomicin-type antibiotics are components from cultures of *Micromonospora carbonaceae*. Flambamycins are produced by *Streptomyces hygrscopicus*. Curamycin A is the primary component of the culture *Streptomyces curacoi*. Avilamycins are the primary components produced by the strain *Streptomyces viridochromgenes*.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. An oligosaccharide antibiotic of the formula:

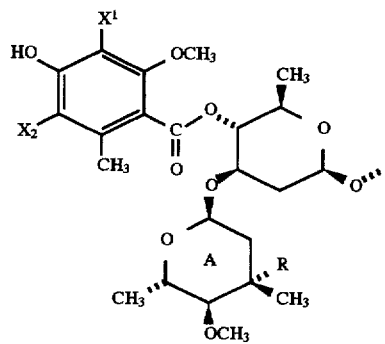

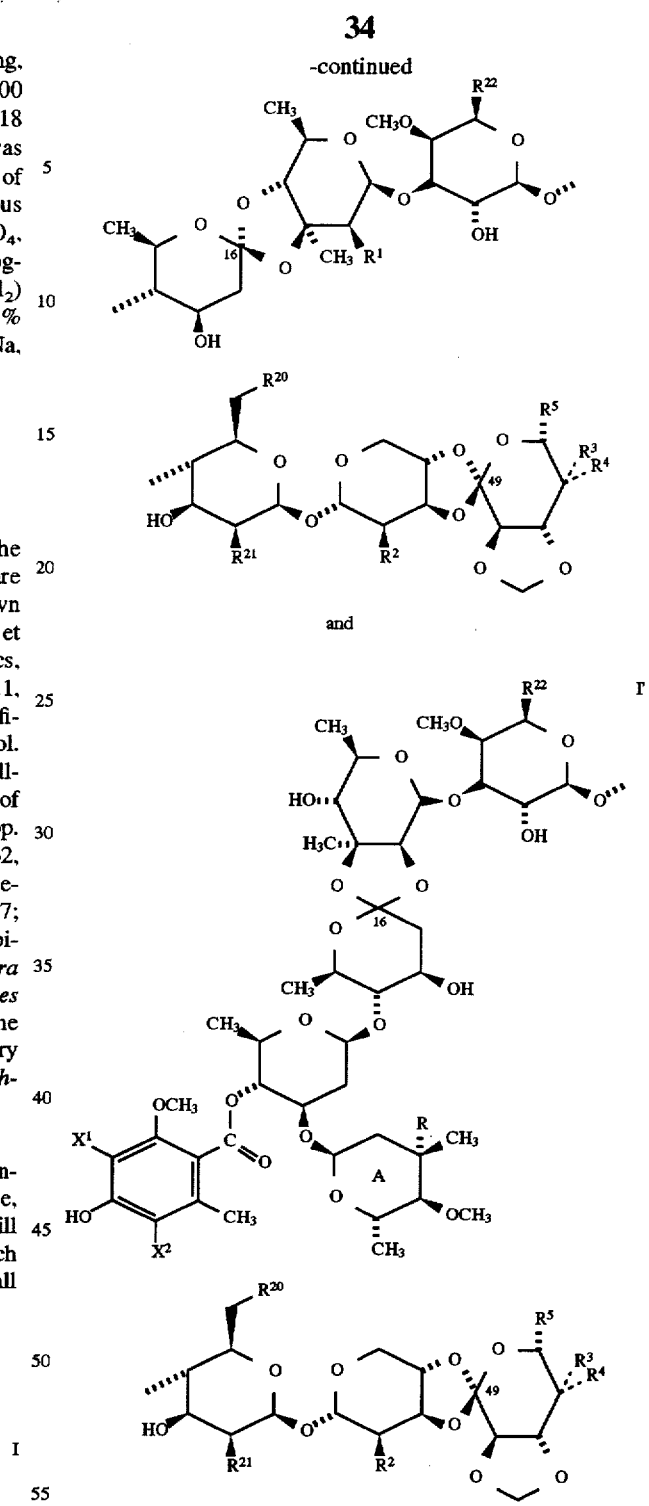

wherein
$X_1$ or $X_2$ independently represent hydrogen or chloro, provided at least one of of $X^1$ and $X^2$ is chloro;
Ring A is as shown or is hydrogen;
R is —OH, —$NO_2$, —$NH_2$, —$NR^6R^7$ or —NHC(O)$CHR^8R^9$,
wherein
$R^6$ is hydrogen or alkyl,
$R^7$ is hydrogen or alkyl,
$R^8$ is hydrogen or —$NR^6R^7$,
wherein $R^6$ and $R^7$ are defined hereinabove, $R^9$ is hydrogen, alkyl or an amino acid side chain,
wherein
$R^{10}$ is hydrogen or alkyl;
$R^{11}$ is hydrogen or alkyl;
$R^1$ is hydrogen or —OH;
$R^2$ is —OH or —$OR^{12}$,
wherein
$R^{12}$ is alkyl or $C(O)R^{13}$,
wherein
$R^{13}$ is alkyl;
$R^3$ is hydrogen,

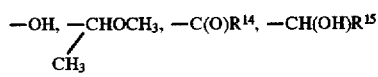

or

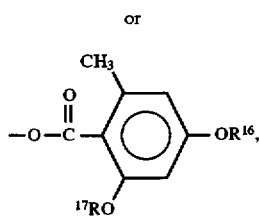

wherein
$R^{14}$ is hydrogen or alkyl,
$R^{15}$ is alkyl,
$R^{16}$ is hydrogen, alkyl or alkenyl,
$R^{17}$ is hydrogen, alkyl or alkenyl,
$R^4$ is hydrogen or OH;
$R^5$ is hydrogen or methyl;
$R^{20}$ is —OH or —$OCH_3$;
$R^{21}$ is —OH or —$OCH_3$;
$R^{22}$ is hydrogen, —$CH_3$ or —$CH_2OH$;
and pharmaceutically acceptable salts thereof.

2. The oligosaccharide antibiotic of claim 1 of formula I.

3. The oligosaccharide antibiotic of claim 1 wherein $X^1$ and $X^2$ are chloro and R is —$NO_2$ or —$NHC(O)CH_3$.

4. The oligosaccharide antibiotic of claim 1 wherein $X^1$ and $X^2$ are chloro and $R^1$ is hydrogen.

5. The oligosaccharide antibiotic of claim 1 wherein $X^1$ and $X^2$ are chloro and $R^1$ is —OH.

6. The oligosaccharide antibiotic of claim 1 wherein $X^1$ and $X^2$ are chloro and $R^2$ is —OH, —$OCH_3$ or —$OCH_2CH_2OH$.

7. The oligosaccharide antibiotic of claim 1 wherein $X^1$ and $X^2$ are chloro and $R^3$ is

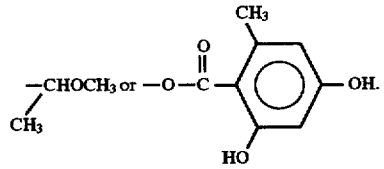

8. The oligosaccharide antibiotic of claim 1 wherein $X^1$ and $X^2$ are chloro and $R^4$ is hydrogen or —OH.

9. The oligosaccharide antibiotic of claim 1 wherein $X^1$ and $X^2$ are chloro and $R^5$ is hydrogen.

10. The oligosaccharide antibiotic of claim 1 wherein $X^1$ and $X^2$ are chloro and $R^{20}$ and $R^{21}$ are —$OCH_3$ and $R^{22}$ is —$CH_3$.

11. The oligosaccharide antibiotic of claim 1 of formula I wherein $X^1$ and $X^2$ are chloro, R is —$NO_2$, $R^1$ and $R^2$ are —OH, $R^3$ is

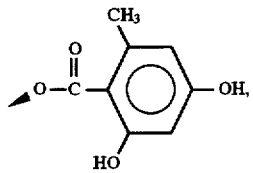

$R^4$ and $R^5$ are hydrogen, $R^{20}$ and $R^{21}$ are —$OCH_3$ and $R^{22}$ is —$CH_3$.

12. The oligosaccharide antibiotic of claim 1 of formula I' wherein $X^1$ and $X^2$ are chloro, R is —$NO_2$, $R^2$ is —OH,
$R^3$ is

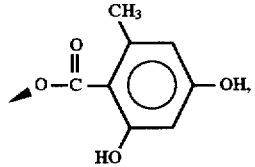

$R^4$ and $R^5$ are hydrogen, $R^{20}$ and $R^{21}$ are —$OCH_3$ and $R^{22}$ is —$CH_3$.

13. The oligosaccharide antibiotic of claim 1 of formula I wherein $X^1$ and $X^2$ are chloro, R is —$NO_2$, $R^1$ is —OH, $R^2$ is —$OCH_2CH_2OH$,
$R^3$ is

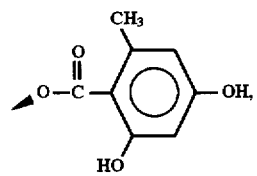

$R^4$ and $R^5$ are hydrogen, $R^{20}$ and $R^{21}$ are —$OCH_3$ and $R^{22}$ is —$CH_3$.

14. The oligosaccharide antibiotic of claim 1 of formula I wherein $X_1$ and $X_2$ are chloro, R is —$NHC(O)CH_3$, $R^1$ and $R^2$ are —OH,
$R^3$ is

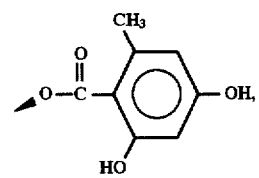

$R^4$ and $R^5$ are hydrogen, $R^{20}$ and $R^{21}$ are —$OCH_3$ and $R^{22}$ is —$CH_3$.

15. The oligosaccharide antibiotic of claim of formula I wherein $X^1$ and $X^2$ are chloro, R is —$NO_2$, $R^1$ is hydrogen, $R^2$ is —$OCH_3$,
$R^3$ is

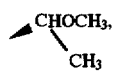

$R^4$ is —OH, $R^5$ is hydrogen, $R^{20}$ and $R^{21}$ are —$OCH_3$ and $R^{22}$ is —$CH_3$.

16. A process for preparing an oligosaccharide antibiotic of the formula:

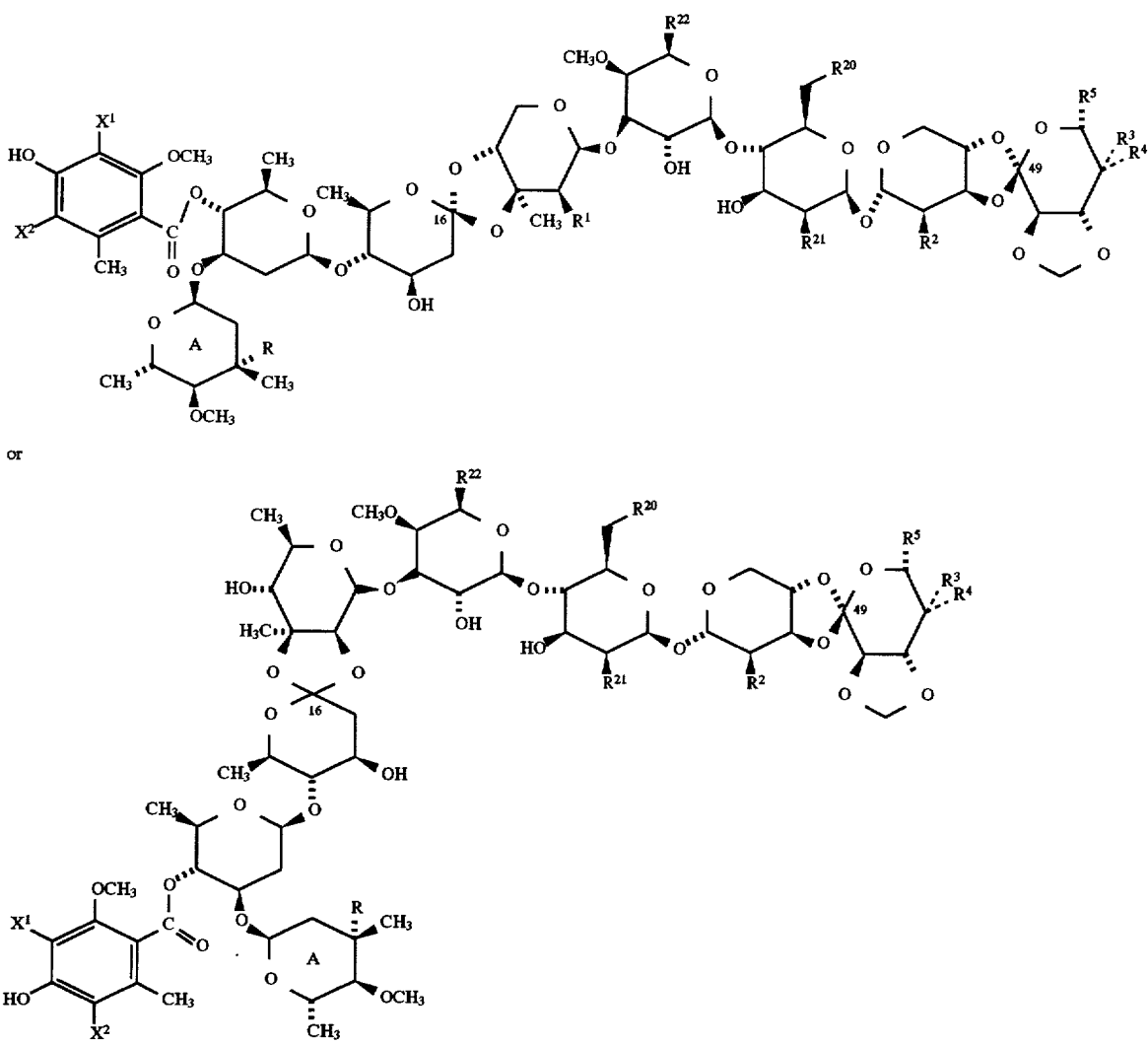

or a mixture thereof, wherein

X¹ and X² independently represent hydrogen or chloro, provided at least one of X¹ and X² is chloro;

Ring A is as shown or is hydrogen;

R is —OH, —NO$_2$, —NH$_2$, —NR$^6$R$^7$ or —NHC(O)CHR$^8$R$^9$, wherein
R$^6$ is hydrogen or alkyl,
R$^7$ is hydrogen or alkyl,
R$^8$ is hydrogen or —NR$^6$R$^7$,
wherein R$^6$ and R$^7$ are defined hereinabove,
R$^9$ is hydrogen, alkyl or an amino acid side chain, wherein
R$^{10}$ is hydrogen or alkyl,
R$^{11}$ is hydrogen or alkyl;

R$^1$ is hydrogen or —OH;

R$^2$ is —OH or —OR$^{12}$,
wherein
R$^{12}$ is alkyl or C(O)R$^{13}$,
wherein
R$^{13}$ is alkyl;

R$^3$ is hydrogen,

—OH, —CH(CH$_3$)OCH$_3$, —C(O)R$^{14}$, —CH(OH)R$^{15}$ or

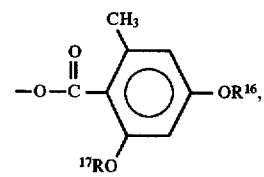

wherein
R$^{14}$ is hydrogen or alkyl,
R$^{15}$ is alkyl,
R$^{16}$ is hydrogen, alkyl or alkenyl,
R$^{17}$ is hydrogen, alkyl or alkenyl, R$^4$ is hydrogen or OH;
R$^5$ is hydrogen or methyl;
R$^{20}$ is —OH or —OCH$_3$;
R$^{21}$ is —OH or —OCH$_3$;
R$^{22}$ is hydrogen, —CH$_3$ or —CH$_2$OH;
and pharmaceutically acceptable salts thereof;
comprising contacting a compound of the formula:

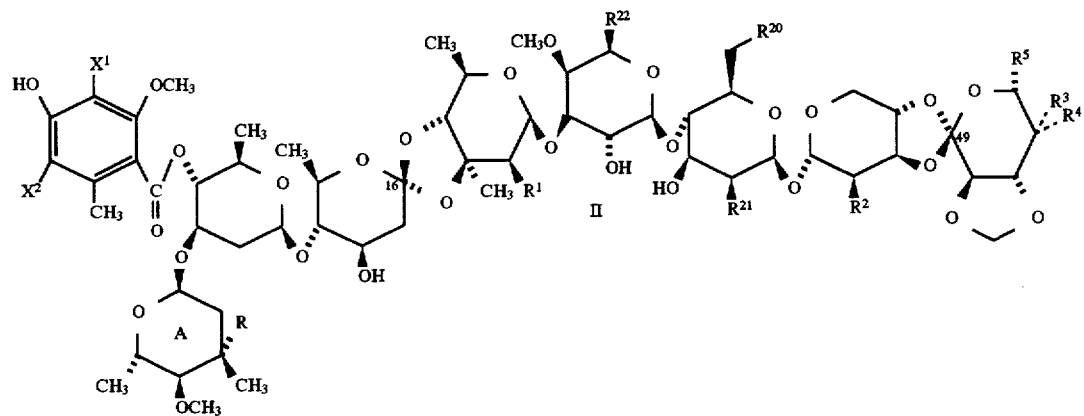

wherein R, $R^1$, $R^2$, $R^3$, $R^4$, $R^5$, $R^{20}$, $R^{21}$ and $R^{22}$ are defined above, with an organic acid and a non-protic solvent under anhydrous conditions to form the oligosaccharide antibiotic of formula I or I' or a mixture thereof.

17. The process of claim 16 wherein the organic acid is p-nitrobenzoic acid.

18. The process of claim 16 wherein the non-protic solvent is tetrahydrofuran.

19. The process of claim 16 wherein the organic acid is p-nitrobenzoic acid and the non-protic solvent is tetrahydrofuran.

* * * * *